(12) United States Patent
Fevola et al.

(10) Patent No.: US 9,060,956 B2
(45) Date of Patent: Jun. 23, 2015

(54) COMPOSITIONS COMPRISING A LOW-DP POLYMERIZED SURFACTANT AND A MICELLAR THICKENER

(75) Inventors: Michael J. Fevola, Belle Mead, NJ (US); Frank C. Sun, Branchburg, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 774 days.

(21) Appl. No.: 12/574,899

(22) Filed: Oct. 7, 2009

(65) Prior Publication Data

US 2011/0082065 A1   Apr. 7, 2011

(51) Int. Cl.
| | |
|---|---|
| A61K 8/81 | (2006.01) |
| A61Q 5/02 | (2006.01) |
| A61Q 19/10 | (2006.01) |
| A61K 8/86 | (2006.01) |
| A61Q 19/00 | (2006.01) |

(52) U.S. Cl.
CPC .............. *A61K 8/8164* (2013.01); *A61K 8/86* (2013.01); *A61K 2800/594* (2013.01); *A61Q 19/00* (2013.01)

(58) Field of Classification Search
CPC .................................. A61Q 5/02; A61Q 19/10
USPC .................... 510/475, 505, 119, 130
See application file for complete search history.

(56) References Cited

U.S. PATENT DOCUMENTS

| | | |
|---|---|---|
| 4,110,263 A | 8/1978 | Lindemann |
| 4,186,113 A | 1/1980 | Verdicchio |
| 4,199,562 A | 4/1980 | Vanlergrghe et al. |
| 4,215,064 A | 7/1980 | Lindemann |
| 4,233,192 A | 11/1980 | Lindemann |
| 4,362,713 A | 12/1982 | Buck |
| 4,430,250 A | 2/1984 | Sebag et al. |
| 4,443,362 A | 4/1984 | Guth |
| 4,450,090 A | 5/1984 | Kinney |
| 4,617,414 A | 10/1986 | Lukenbach |
| 4,664,835 A | 5/1987 | Grollier et al. |
| 4,726,915 A | 2/1988 | Verdicchio |
| 4,879,107 A | 11/1989 | Vanlerberghe et al. |
| 5,192,462 A | 3/1993 | Gloor et al. |
| 6,090,395 A * | 7/2000 | Asmus et al. .................. 424/401 |
| 6,210,689 B1 | 4/2001 | Martino et al. |
| 6,358,914 B1 | 3/2002 | Gabriel et al. |
| 6,610,315 B2 * | 8/2003 | Scholz et al. .................. 424/405 |
| 6,627,612 B1 | 9/2003 | O'Lenick, Jr. et al. |
| 7,417,020 B2 * | 8/2008 | Fevola et al. .................. 510/475 |
| 7,446,087 B2 * | 11/2008 | Fevola et al. .................. 510/475 |
| 7,446,088 B2 * | 11/2008 | Fevola et al. .................. 510/475 |
| 2004/0223925 A1 | 11/2004 | L'Alloret |
| 2005/0070453 A1 | 3/2005 | LiBrizzi et al. |
| 2005/0075256 A1 | 4/2005 | Librizzi |
| 2005/0186159 A1 | 8/2005 | Gonzalez et al. |
| 2006/0099165 A1 * | 5/2006 | Barbeito et al. ........... 424/70.13 |
| 2006/0257348 A1 | 11/2006 | Walters et al. |
| 2007/0259796 A1 * | 11/2007 | Fevola et al. .................. 510/130 |
| 2007/0259798 A1 | 11/2007 | Fevola et al. |

FOREIGN PATENT DOCUMENTS

| | | |
|---|---|---|
| EP | 0308031 B1 | 4/1993 |
| EP | 0962221 | 12/1999 |
| EP | 2018890 A2 | 1/2009 |
| WO | WO 01/23515 A1 | 9/1999 |
| WO | WO 2006/018324 A | 2/2006 |

OTHER PUBLICATIONS

Definition from Glossary of Basic Terms in Polymer Science, A.D. Jenkins et al. *Pure Appl. Chem.* 1996 68, 2287-2311.
Sagarin, Cosmetics, Science and Technology, 2$^{nd}$ Edition, vol. 1, pp. 32-43 (1972).
The International Cosmetic Ingredient Dictionary and Handbook, eds. Wenninger and Mc Ewen, pp. 1656-61, 1626, and 1654-55 (The Cosmetic, Toiletry, and Fragrance Assoc., Washington, D.C., 7. sup. Th Edition, 1997).
Colonial Chemicals, Inc., Polysuga® Nate—Sulfonated Poly (Alkyl Polyglucosides) Low Irritation Sulfonates.
Database GNPD [Online] MINTEL; Jul. 2009, "Sport face sunblock lotion SPF70+", XP002713711, Database accession No. 1142706.
Database GNPD [Online] MINTEL; Aug. 2002, "Lotion spray", XP002713712, Database accession No. 10115337.

* cited by examiner

*Primary Examiner* — Nicole M Buie-Hatcher
*Assistant Examiner* — M. Reza Asdjodi

(57) ABSTRACT

Provided are healthcare compositions comprising a low-DP polymerized surfactant, a micellar thickener, and a cosmetically-acceptable or pharmaceutically-acceptable carrier. Also, provided are methods of cleansing or treating a mammal by applying healthcare compositions of the present inventions to the mammalian body.

17 Claims, 1 Drawing Sheet

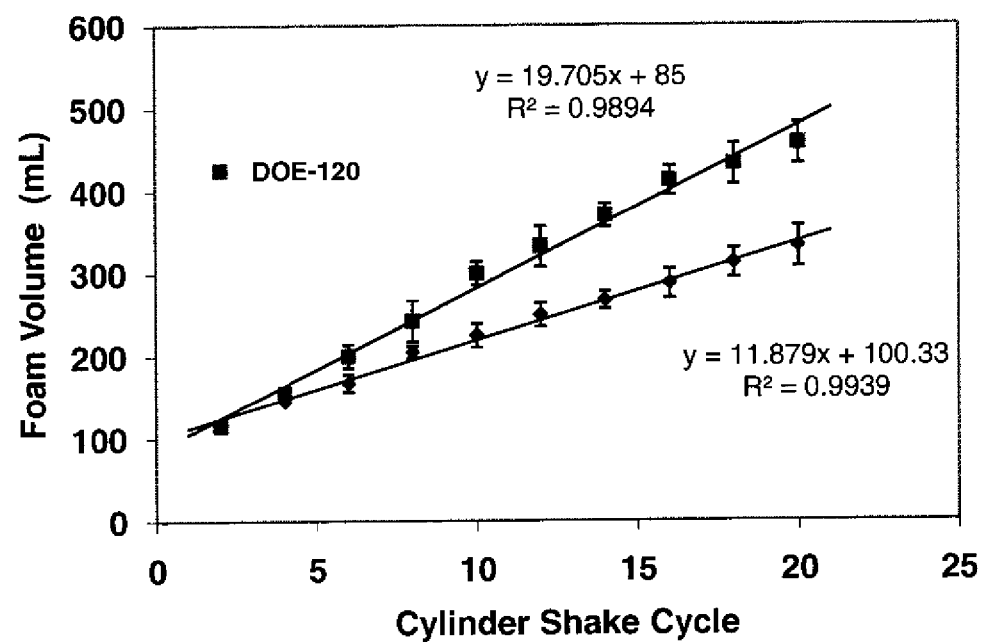

US 9,060,956 B2

COMPOSITIONS COMPRISING A LOW-DP POLYMERIZED SURFACTANT AND A MICELLAR THICKENER

FIELD OF INVENTION

The present invention relates to compositions comprising low-DP polymerized surfactants and, in particular, compositions comprising low-DP polymerized surfactants that are useful in healthcare applications and have relatively low irritation and high flash-foaming associated therewith.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to use combinations and levels of surfactants sufficient to achieve relatively high foam volume and/or foam stability.

However, as is recognized in the art, synthetic detergents tend to be irritating to the skin and eyes. Thus, as levels of such detergents are increased in attempts to increase cleansing and foaming properties associated with certain compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating), with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance. Yet another approach described in, Librizzi et al., (in United States Published Patent Application US20050075256 A1) discusses the use of a composition including both a hydrophobically modified polymer and a surfactant to provide low irritation cleansing composition.

Still another approach to producing mild cleansing compositions is to use polymerized surfactants having a relatively low degree-of-polymerization and at least about 10 mol % amphiphilic repeat units. See U.S. Pat. No. 7,417,020.

However, while improvements have made been in mildness, the inventors have recognized that additional improvements in mildness are desirable, particularly improvements in both mildness and the ability of compositions to provide exceptional so-called "flash foam," i.e., the ability to form a high volume of foam with relatively low amount of energy input.

BRIEF DESCRIPTION OF THE DRAWING

FIG. 1 is a graph of the foam generation rate of a composition of the present invention and a comparative example.

SUMMARY OF THE INVENTION

The present invention provides personal care compositions that overcome the disadvantages of the prior art and have relatively low irritation properties and high flash foam associated therewith. In particular, applicants have discovered that low-DP polymerized surfactants may be combined with micellar thickeners to produce compositions having low irritation and high flash foam associated therewith.

According to one aspect, the present invention provides a personal care composition comprising a low-DP polymerized surfactant and a micellar thickener.

In yet another aspect of the invention, applicants have provided a method of treating the skin, hair, or vaginal region, the method comprising applying to the skin, hair, or vaginal region a composition comprising a low-DP polymerized surfactant and a micellar thickener.

DESCRIPTION OF PREFERRED EMBODIMENTS

All percentages listed in this specification are percentages by weight, unless otherwise specifically mentioned.

As used herein, the term "healthcare" refers to the fields of personal care and medical care including, but not limited to, infant care, oral care, sanitary protection, skin care, including the treatment of adult or infant skin to maintain the health of the skin, improve the health of the skin, and/or improve the appearance of the skin, wound care, including the treatment of a wound to assist in the closure or healing of a wound, and/or to reduce the pain or scarring associated with the wound, women's health, including the treatment of tissue in the internal or external vaginal area and/or breast, maintaining or improving the health of such tissue or skin, repairing such tissue or skin, reducing irritation of such tissue or skin, maintaining or improving the appearance of such tissue or skin, and improving or enhancing sexual function associated with such tissue or skin, and the like.

As noted above, applicants have discovered unexpectedly that by combining a low-DP polymerized surfactant with a micellar thickener one can form a composition that has both low irritation and high amounts of flash foam thereby greatly enhancing the aesthetic appeal of the composition.

Applicants have noted a surprisingly strong ability of micellar thickeners to thicken a composition having a low-DP polymerized surfactant and further allow the composition to quickly reduce viscosity upon dilution with water.

Without wishing to be bound by theory, upon investigation of Applicant's discovery, Applicants believe that the low-DP polymerized surfactant is readily incorporated at the molecular level into the worm-like micelles whose formation is encouraged by the micellar thickener. The "intermolecular thickening network" thereby created is highly concentration sensitive, and thus, "breaks" readily upon dilution, allowing strong flash foam performance. This ability to disrupt the network upon dilution is particularly important for compositions which are reliant upon the low-DP polymerized surfactant to generate foam, since low-DP polymerized surfactants are larger and generally more slowly diffusing than conventional surfactants. This lack of mobility would otherwise reduce the ability of the low-DP polymerized surfactant to generate flash foam.

As used herein the term "polymerized surfactant" refers to any polymer including repeat units that are amphiphilic, i.e. the repeat units include at least one hydrophilic moiety and at least one hydrophobic moiety.

A "repeat unit" as defined herein and known the art is the smallest atom or group of atoms (with pendant atoms or groups, if any) comprising a part of the essential structure of a macromolecule, oligomer, block, or chain, the repetition of which constitutes a regular macromolecule, a regular oligomer molecule, a regular block, or a regular chain (definition from Glossary of Basic Terms in Polymer Science, A. D. Jenkins et al. *Pure Appl. Chem.* 1996 68, 2287-2311.) As will be recognized by those of skill in the art in light of the description herein and knowledge of the art, the backbone of a polymer derived from ethylenically-unsaturated monomers comprises repeat units including one or two, or in the case of alternating polymers four, carbon atoms that were unsaturated in the monomers prior to polymerization, and any pendant groups of such carbons. For example, polymerization of an ethylenically-unsaturated monomer of the formula: (A)(Y)C═C(B)(Z) will generally result in a polymer comprising repeat units of the formula:

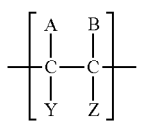

comprising the two previously unsaturated carbons of the monomer and their pendant groups (examples of which are described herein below, for example in the descriptions of SRUs, ARUs, and HRUs.) However, if the pendant groups of the two carbons are the same such that, for example in the formula above, A-C—Y and B—C—Z are the same moiety, then each of such one carbon units and its pendant groups (A-C—Y or B—C—Z, being the same) are considered to be the repeat unit comprising only one previously unsaturated carbon from the monomer (e.g. the repeat unit of a homopolyer derived from ethylene, $H_2C═CH_2$ is [—[$CH_2$]—] not [—[$CH_2CH_2$]—]. With regard only to alternating copolymers, which as known in the art are defined as those polymers in which the repeat units derived from the two comonomers alternate consistently throughout the polymer (as opposed to the random polymerization of co-monomers to form a polymer in which repeat units derived from the two monomers are randomly linked throughout the polymer or the block copolymerization of comonomers to form non-alternating blocks of repeat units derived from the two monomers), the repeat unit is defined as the unit derived from one of each of the co-monomers comprising four carbons that were previously ethylenically-unstaurated in the two comonomers prior to polymerization. That is, maleic anhydride and vinyl methyl ether are used in the art to form an alternating copolymer, poly(maleic anhydride-alt-vinyl methyl ether) having repeat units of the structure:

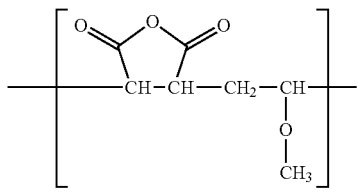

For saccharide-based polymers whose backbone is formed by linking sugar rings, the repeat unit generally comprises the sugar ring and pendant groups (as shown herein below, for example in the descriptions of SRUs, ARUs, and HRUs.) Examples of such repeat units also include sugar ring repeat units with pendant sugar rings, for example, Glactomannans are polysaccharides comprised of a mannose (monosaccharide-based) backbone. Pending from some but not all of the mannose groups in the backbone (and arranged in either a random or block fashion) are pendant galactose groups. As will be readily understood by one skilled in the art, this structure is best described as having, two repeat units, mannose and mannose-galactose.

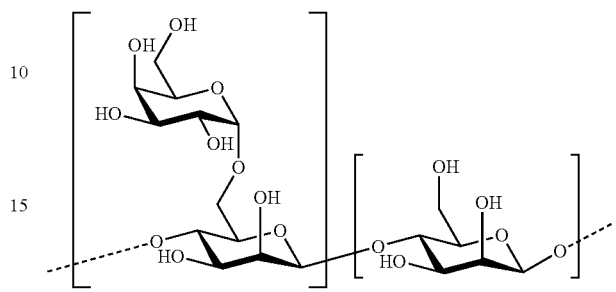

For alternating saccharide-based polymers, then the repeat unit is the two sugar rings derived from the alternating sugar-based monomers and their pendant groups. For example, Hyaluronan is an alternating saccharide copolymer derived from two saccharides, D-glucuronic acid and D-N-acetylglu-cosamine that alternate to give a disaccharide repeat units.

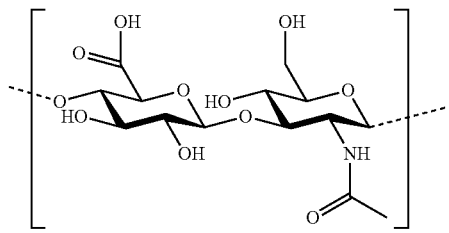

A "hydrophobic moiety" is hereby defined as a nonpolar moiety that contains at least one of the following: (a) a carbon-carbon chain of at least four carbons in which none of the four carbons is a carbonyl carbon or has a hydrophilic moiety bonded directly to it; (b) two or more alkyl siloxy groups (—[Si(R)$_2$—O]—); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly(oxybutylene), poly(dimethylsiloxane), fluorinated hydrocarbon groups containing a carbon chain of at least four carbons in which none of the four carbons has a hydrophilic moiety bonded directly to it, and the like.

A "hydrophobic moiety" is hereby defined as a nonpolar moiety that contains at least one of the following: (a) a carbon-carbon chain of at least four carbons in which none of the four carbons is a carbonyl carbon or has a hydrophilic moiety bonded directly to it; (b) two or more alkyl siloxy groups (—[Si(R)$_2$—O]—); and/or (c) two or more oxypropylene groups in sequence. A hydrophobic moiety may be, or include, linear, cyclic, aromatic, saturated or unsaturated groups. In certain preferred embodiments, hydrophobic moieties comprise a carbon chain of at least six or more carbons, more preferably seven or more carbons in which none of the carbons in such chain have a hydrophilic moiety bonded directly thereto. Certain other preferred hydrophobic moieties include moieties comprising a carbon chain of about eight or more carbon atoms, more preferably about 10 or more carbon atoms in which none of the carbons in such chain have a hydrophilic moiety bonded directly thereto. Examples of hydrophobic functional moieties may include esters, ketones, amides, carbonates, urethanes, carbamates, or xanthate functionalities, and the like, having incorporated therein or attached thereto a carbon chain of at least four carbons in which none of the four carbons has a hydrophilic moiety bonded directly to it. Other examples of hydrophobic moieties include groups such as poly(oxypropylene), poly(oxybutylene), poly(dimethylsiloxane), fluorinated hydrocarbon groups containing a carbon chain of at least four carbons in which none of the four carbons has a hydrophilic moiety bonded directly to it, and the like.

As defined herein, the term, "low-DP polymerized surfactant," refers to a polymerized surfactant, as defined above, which further meets the following criteria (a) and (b): (a) the polymerized surfactant has at least about 7 and less than about 2000 amphiphilic repeat units on a weight average basis; and (b) the amphiphilic repeat units comprise at least about 10 mole % of the polymerized surfactant. Examples of certain preferred low-DP polymerized surfactants included those having 7 to about 2000 amphiphilic repeat units, such as from 10 to about 1000 amphiphilic repeat units, and even more preferably from about 20 to about 500 amphiphilic repeat units. In certain embodiments, the low-DP polymerized surfactants of the present invention preferably comprise least about 25 mole % of amphiphilic repeat units.

As will be recognized by one of skill in the art, the pattern of repeat units incorporated in low-DP polymerized surfactants of the present invention are generally random; however, they may also have alternating, statistical, or blocky incorporation patterns. In addition, low-DP polymerized surfactants architectures may be linear, star-shaped, branched, hyperbranched, dendritic, or the like.

The molecular weight of the low-DP polymerized surfactant is not critical. In one embodiment of the invention, the polymerized surfactant has a molecular weight from about 3500 to about 500,000. In a preferred embodiment, the polymerized surfactant has a molecular weight from about 5000 to about 200,000, more preferably from about 7500 to about 100,000, and most preferably from about 10,000 to about 50,000.

Any of a variety of polymerized surfactants that meet the above criteria may be suitable for the present invention. Polymerized surfactants suitable for use in the present invention include polymerized surfactants of various chemical classifications and obtained via a variety of synthetic routes. Examples include polymers having a backbone that substantially comprises a plurality of carbon-carbon bonds, preferably essentially consists or consists only of carbon-carbon bonds and polymers having a backbone comprising a plurality of carbon-heteroatom bonds (as will be recognized by those of skill in the art, the backbone refers generally to the portion of repeat units in a polymer that is covalently bonded to adjacent repeat units (vs. "pendant groups")). Examples of suitable polymers having a backbone consisting essentially of carbon-carbon bonds and polymers comprising carbon-heteroatom bonds include the following, as well as, combinations of two or more thereof, and the like:

[I.] Polymers having a backbone that substantially comprises carbon-carbon bonds such as may be (1) formed from ethylenically (or acetylenically) unsaturated monomers or (2) polyketones (in all subclasses (A)-(D) hereunder, n=7 to 2,000 and m is up to 10,000):

Subclass (A): Homopolymerization of prefabricated reactive amphiphiles containing ethylenically unsaturated functionalities (hereinafter "EUAHs").

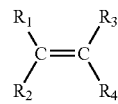

where $R_1=R_2=H$, $R_3=H$ or $CH_3$, and $R_4$ comprises Amphiphilic (Amphil) group, or where $R_1=R_2=H$, $R_3$ comprises a hydrophilic group (Hphil), and $R_4$ comprises hydrophobic group (Hphob), or where $R_1$, $R_3$ are independently H or $CH_3$, $R_2$ comprises Hphil, and $R_4$ comprises Hphob group, or where $R_1$, $R_4$ are independently H or $CH_3$, $R_3$ comprises Hphil, and $R_4$ comprises Hphob group, or where $R_2$, $R_3$ are independently H or $CH_3$, $R_1$ comprises Hphil, and $R_4$ comprises Hphob group to yield a polymerized surfactant with an amphiphilic repeat unit shown in brackets immediately below, and having a number of amphiphilic repeat units, n:

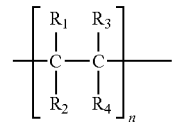

Examples of monomers useful for making this class of polymerized surfactants include:

Anionic:

ω-alkeneoates: e.g. sodium 11-undecenoate

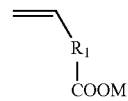

where $R_1$=any linear or branched carbon chain containing more than 5 carbon atoms and M=H$^+$, NH$_4^+$, or any Group IA alkali metal cation.

(Meth)acrylamidoalkylcarboxylates and (meth)acryloyloxyalkylcarboxylates: e.g. sodium 11-acrylamidoundecanoate, sodium 11-methacryloyloxyundecanoate

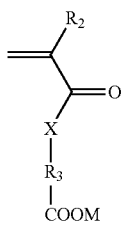

where $R_2$=H or $CH_3$, X=O or NH, $R_3$=any linear or branched carbon chain containing more than 5 carbon atoms and M=$H^+$, $NH_4^+$, or any Group IA alkali metal cation.

(Meth)acrylamidoalkylsulfonic acids: e.g. 2-acrylamido-dodecylsulfonic acid

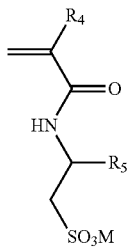

where $R_4$=H or $CH_3$, X=O or NH, $R_5$=any linear or branched carbon chain containing more than 5 carbon atoms and M=$H^+$, $NH_4^+$, or any Group IA alkali metal cation.

Allylalkylsulfosuccinates: e.g. sodium allyldodecylsulfo-succinate (TREM LF-40, Cognis)

Allylalkylsulfosuccinates

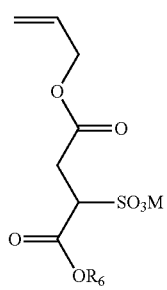

where $R_6$=any linear or branched carbon chain containing more than 5 carbon atoms and M=$H^+$, $NH_4^+$, or any Group IA alkali metal cation.

Cationic:
Quaternized aminoalkyl(meth)acrylamides and aminoalkyl(meth)acrylates: e.g. (3-methacrylamidopropyl) dodecyldimethylammonium chloride, (2-methacryloyloxyethyl)dodecyl dimethylammonium chloride

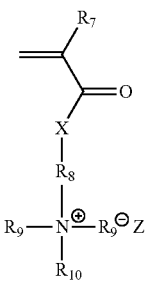

where $R_7$=H or $CH_3$, X=O or NH, $R_8$=any linear or branched carbon chain containing 5 or less carbon atoms, $R_9$=H, $CH_3$, $CH_2CH_3$ or $CH_2CH_2OH$, $R_{10}$=any linear or branched carbon chain containing more than 5 carbon atoms and Z=any Group VII-A halide anion, OR where $R_7$=H or $CH_3$, X=O or NH, $R_8$=any linear or branched carbon chain containing more than 5 carbon atoms, $R_9$, $R_{10}$ are independently H, $CH_3$, $CH_2CH_3$ or $CH_2CH_2OH$, and Z=any Group VII-A halide anion Quaternized vinylpyridines: e.g. (4-vinyl)dodecylpyridinium bromide

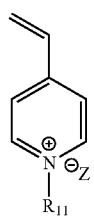

where $R_{11}$=any linear or branched carbon chain containing more than 5 carbon atoms and Z=any Group VII-A halide anion.

Alkyldiallylmethylammonium halides: e.g. diallyldodecylmethylammonium chloride

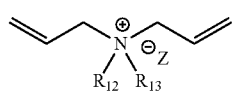

where $R_{12}$=H, $CH_3$ or $R_{13}$, $R_{13}$=any linear or branched carbon chain containing more than 5 carbon atoms and Z=any Group VII-A halide anion.

Zwitterionic:
Ammonioalkanecarboxylates: e.g. 2-[(11-(N-methylacrylamidyl)undecyl)dimethylammonio]acetate

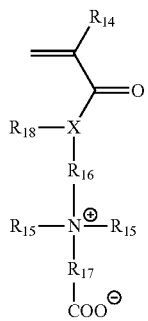

where $R_{14}$=H or $CH_3$, X=O or N, $R_{15}$=H, $CH_3$, $CH_2CH_3$ or $CH_2CH_2OH$, $R_{16}$=any linear or branched carbon chain more than 5 carbon atoms, $R_{17}$=any linear or branched carbon chain containing 5 or less carbon atoms, and $R_{18}$=H, $CH_3$, or nothing.

Ammonioalkanesulfonates: e.g. 3-[(11-methacryloyloxyundecyl)dimethylammonio]propanesulfonate

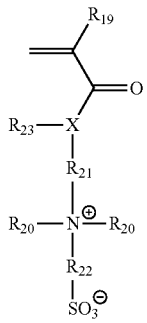

where $R_{19}$=H or $CH_3$, X=O or N, $R_{20}$=H, $CH_3$, $CH_2CH_3$ or $CH_2CH_2OH$, $R_{21}$=any linear or branched carbon chain more than 5 carbon atoms, $R_{22}$=any linear or branched carbon chain containing 5 or less carbon atoms, and $R_{23}$=H, $CH_3$, or nothing.

Nonionic:
ω-methoxypoly(ethyleneoxy)alkyl-α-(meth)acrylates:
e.g. ω-methoxypoly(ethyleneoxy)undecyl-α-methacrylate

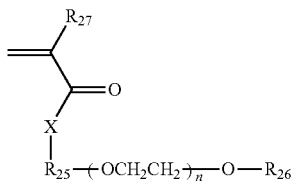

where $R_{24}$=H or $CH_3$, X=O, $R_{25}$=any linear or branched carbon chain more than 5 carbon atoms, n is an integer from about 4 to about 800, and $R_{26}$=any linear or branched carbon chain containing 5 or less carbon atoms ω-alkoxypoly(ethyleneoxy)-α-(meth)acrylates and ω-alkoxypoly(ethyleneoxy)-α-itaconates: e.g. steareth-20 methacrylate, ceteth-20 itaconate

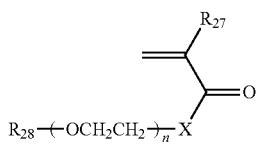

where $R_{27}$=H, $CH_3$, or $CH_2COOH$, X=O, $R_{28}$=any linear or branched carbon chain more than 5 carbon atoms, and n is an integer from about 4 to about 800

Subclass (B): Copolymerization of one or more prefabricated reactive amphiphiles containing ethylenically unsaturated functionalities from above with another reactive amphiphilie from subclass (A) above and/or with one or more ethylenically unsaturated hydrophilic comonomers of the formula (hereinafter "EUACs"):

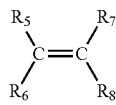

where $R_5$=$R_6$=H, $R_7$=H or $CH_3$, and $R_8$ comprises HPhil group, or where $R_5$, $R_6$ are independently H or $CH_3$, $R_7$ comprises HPhil group, and $R_8$ comprises HPhil group where $R_5$, $R_7$ are independently H or $CH_3$, $R_6$ comprises HPhil group, and $R_8$ comprises HPhil group where $R_6$, $R_7$ are independently H or $CH_3$, $R_5$ comprises HPhil group, and $R_8$ comprises HPhil group to yield a polymerized surfactant with an amphiphilic repeat unit shown in brackets immediately below, and having a number of amphiphilic repeat units, n and a number of non-amphiphilic repeat units, m:

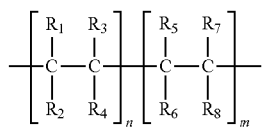

Examples of prefabricated reactive amphiphiles containing ethylenically unsaturated functionalities are described above with reference to (A). Examples of hydrophilic comomomers that may reacted therewith include:

i) Nonionic: acrylamide, N,N-dimethylacrylamide, N-vinylformamide, hydroxyethyl(meth)acrylate, glyceryl methacrylate, sucrose mono(meth)acrylate, ω-methoxypoly(ethyleneoxy)-α-(meth)acrylate ii) Anionic: acrylic acid, 2-acrylamido-2-methylpropanesulfonic acid, 3-acrylamido-3-methylbutanoic acid iii) Cationic: N,N-dimethylaminoethyl methacrylate, N,N-dimethylpropyl (meth)acrylamide, (3-(meth)acrylamidopropyl)trimethylammonium chloride, diallyldimethylammonium chloride iv) Zwitterionic: 3-[(3-(meth)acrylamidopropyl)dimethylammonio]propanesulfonate, 3-(3-(meth)acrylamidopropyldimethylammonio)propionate, 3-(3-(meth)acrylamidopropyldimethylammonio)acetate Subclass (C): Polymerization of multifunctional amphiphilic molecules with multifunctional linking agents (for example, the step-growth polymerization of alkyl(poly) glucosides with difunctional linkers such as dicarboxylic acids, bis(acyl halide)s, diisocyanates, bis(epoxide)s, or epichlorihydrin) yielding a polymerized surfactant with an amphiphilic repeat unit shown in brackets below, and having a number of amphiphilic repeat units, n (hereinafter "step-growth amphiphiles" or "SGAs"):

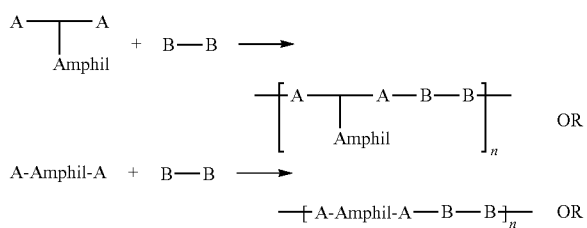

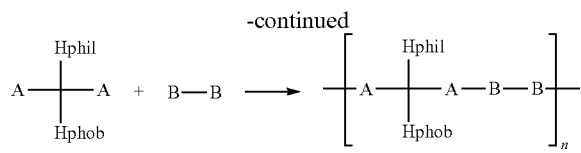

Subclass (D): Post-polymerization modification of precursor polymers to render some or all repeat units amphiphilic; yielding a polymerized surfactant with an amphiphilic repeat unit shown in brackets below, and having a number of amphiphilic repeat units, n and a number of non-amphiphilic repeat units, m (hereinafter "PPDAs"):

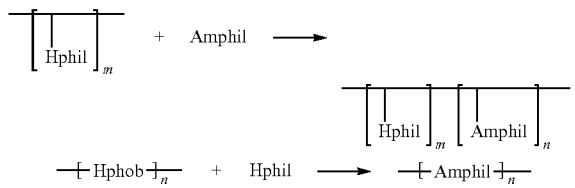

Examples are indicated below:
  v) Via post-polymerization modification to render repeat units amphiphilic:
    (a) Hydrolysis of 1:1 alternating copolymers of maleic anhydride and long chain α-olefins or alkyl vinyl ethers
    (b) Ring-opening of 1:1 alternating copolymers of maleic anhydride and long chain α-olefins or alkyl vinyl ethers with aminoalkylsulfonic acids, aminoalkylcarboxylic acids or dialkylaminoalkylamines
  vi) Via post-polymerization modification to incorporate amphiphilic repeat units:
    (a) Reaction of polymer with repeat units comprising hydroxyl functionalities, such as polyvinylalcohol, hydroxyethylcellulose, or dextran, with 3-chloro-2-hydroxypropylalkyldimethylammonium chlorides, such as QUAB 342, 360, and 426 commercially available from Degussa AG of Parsippany, N.J.
    (b) Partial quaternization of poly(4-vinylpyridine) with alkylbromides Examples of suitable polymerized surfactants having a backbone comprised of carbon-heretoatom bonds include SGAs and PPDAs having such a backbone, such as, polyethers, including polysaccharides, polyesters, polycarbonates, polyanhydrides, polyamides, polyurethanes, polyureas, polyimides, polysufones, polysulfides, combinations of two or more thereof, and the like.

According to certain preferred embodiments, the polymerized surfactant for use in the present invention comprise EUAHs, such as Poly (sodium allyldodecylsulfosuccinate), and the like, EUACs, such as Poly(acrylic acid co-2-acrylamideodododecylsulfonic acid), Poly (sodium allyldodecyl sulfosuccinate-co-acrylic acid), and the like, carbon-carbon backbone PPDA polymers such as octadecene/maleic anhydride copolymers, tetradecene/maleic anhydride copolymers, derivatives thereof (including, for example, hydrolyzed derivatives, amidated derivatives, and the like), combinations of two or more thereof, and the like.

In certain other preferred embodiments, the polymerized surfactants for use in the invention comprise carbon-heteroatom backbone polymers, such as, polysaccharides, polyesters, polycarbonates, polyanhydrides, polyamides, polyurethanes, polyureas, polyimides, polysufones, polysulfides, combinations of two or more thereof. Certain preferred carbon-heteroatom backbone polymers include polysaccharides.

Furthermore, applicants have found that according to certain embodiments of the invention, suitable low-DP polymerized surfactants, when tested in dynamic light scattering (DLS), have a PMOD % of less than about 90%, more preferably less than about 80%, more preferably less than about 50%, and more preferably less than about 40%, are useful in producing compositions having beneficially low irritation properties associated therewith. As is described in U.S. Pat. No. 7,417,020, entitled, "COMPOSITIONS COMPRISING LOW-DP POLYMERIZED SURFACTANTS AND METHODS OF USE THEREOF," issued to Fevola et al., commonly assigned, and herein incorporated by reference in its entirety, PMOD % is calculated using the "average micelle hydrodynamic diameter $d_H$," a measure of average micelle size. The "fraction of micelles with $d_H$<9 nanometers (nm)" provides a measurement of the degree of irritation that may result from compositions that include surfactants. Surfactant micelles are rarely monodisperse in size and aggregation number (i.e., the average number of molecules of surfactant in a particular micelle). Instead, surfactant micelles tend to exist as a population with distributions of sizes and aggregation numbers that give rise to micelle size distribution functions. The "fraction of micelles with $d_H$<9 nanometers (nm)" is thus a measure of the capability of providing a distribution of micelles that, is "shifted" to favor larger micelles.

Any amounts of low-DP polymerized surfactants suitable to, for example, produce micelle size distributions of the present invention may be combined according to the present methods. According to certain embodiments, low-DP polymerized surfactant is used in a concentration from greater than about 0.1% to about 30% by weight of active polymerized surfactant in the composition. Preferably, low-DP polymerized surfactant is in a concentration from about 0.5 to about 20%, more preferably from about 1 to about 15%, even more preferably from about 2 to about 10% of active polymerized surfactant in the composition. In certain other preferred embodiments, the compositions of the present invention comprise from about 0.5 to about 15%, more preferably from about 1.5 to about 10%, even more preferably from about 2 to about 7%, even more preferably from about 3 to about 7% of active polymerized surfactant in the composition.

As further noted above, applicants have discovered unexpectedly that by combining a low-DP polymerized surfactant with a micellar thickener one can form a composition that has both low irritation and high amounts of flash foam, thereby greatly enhancing the aesthetic appeal of the composition.

As defined herein, the term, "micellar thickener," as will be readily understood by one skilled in the art, refers to a polymer that meets one or both of the two criteria described below. According to the first criteria, (I): the micellar thickener is a polymer that includes at least three hydrophilic repeat units or superhydrophilic repeat units, and further includes two or more independent hydrophobic moieties, and wherein the polymer has a relatively low weight-average molecular weight, e.g., less than about 100,000, preferably less than about 50,000, more preferably less than about 25,000, most preferably less than about 10,000. Preferred hydrophobic moieties include 10 or more carbon atoms, more preferably from 12 to 30 carbon atoms, even more preferably from 16 to 26 carbon atoms, and most preferably from 18 to 24 carbon atoms. Micellar thickeners that meet criteria (I) are generally believed to be suitable for modifying the corona (periphery)

of surfactant micelles and, for convenience will hereinafter be referred to as "corona thickeners."

According to the second criteria, (II): the micellar thickener is a compound that includes at least two non-ionic hydrophilic moieties; and includes either (a) two or more hydrophobic moieties that have a carbon chain that comprises 8 or more carbon atoms; or (b) one or more hydrophobic moieties that have a carbon chain that comprises 12 or more carbon atoms; and has a molecular weight less than about 5,000 (daltons), preferably less than about 3,000, more preferably less than about 2,000, most preferably less than about 1500. Micellar thickeners that meet criteria (II) are generally believed to be suitable for modifying the core (center) of surfactant micelles and, for convenience will hereinafter be referred to as "core thickeners."

Hydrophilic moieties are defined above with respect to low-DP polymerized surfactants. Preferred hydrophilic moieties include nonionics such as hydroxyl and ethyleneoxy.

As will be readily understood by those of skill in the art, the term "hydrophilic repeat unit," ("HRU") is defined as a repeat unit that comprises one and only one hydrophilic moiety and no hydrophobic moieties. For example, HRUs may be derived from ethylenically-unsaturated monomers having at least one hydrophilic moiety and no hydrophobic moieties, including repeat units of the general formulae

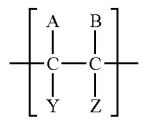

wherein A, B, Y, and Z collectively include one and only one hydrophilic moiety and no hydrophobic moieties; or

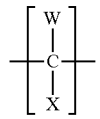

wherein W and X collectively include one and only one hydrophilic moiety and no hydrophobic moieties, examples of which include

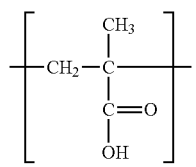

methacrylic acid hydrophilic repeat unit (HRU); and the like.

Other examples of HRUs include sugar-based, monosaccharide repeat units including repeat units derived from fructose, glucose, galactose, mannose, glucosamine, mannuronic acid, guluronic acid, and the like, such as:

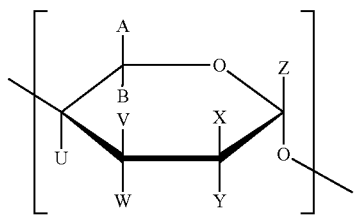

wherein A, B, U, V, W, X, Y, and Z collectively include one and only one hydrophilic moiety and no hydrophobic moieties, or

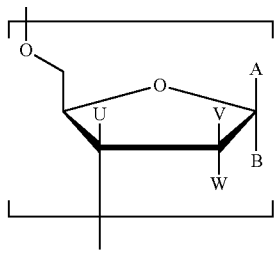

wherein A, B, U, V, and W collectively include one and only one hydrophilic moiety and no hydrophobic moieties. One example of saccharide-based hydrophilic repeat unit includes methylcellulose HRU, (methyl-substituted poly[β(1→4)-D-glucose], DS=2.0)

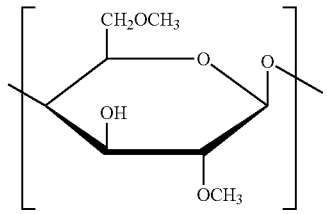

Other examples of HRUs include repeat units derived from amino acids, including, for example, repeat units of the formula:

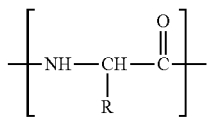

wherein R is neither a hydrophilic nor hydrophobic moiety, one example of which includes

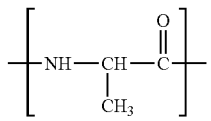

alanine HRU; and the like. As will be recognized by one of skill in the art, in any of the formulae herein, examples of moieties that are neither hydrophilic nor hydrophobic include hydrogen, $C_1$-$C_3$ alkyl, $C_1$-$C_3$ alkoxy, $C_1$-$C_3$ acetoxy, and the like.

As used herein, the term "superhydrophilic repeat unit," ("SRU") is defined as a repeat unit that comprises two or more hydrophilic moieties and no hydrophobic moieties. For example, SRUs may be derived from ethylenically-unsaturated monomers having two or more hydrophilic moieties and no hydrophobic moieties, including repeat units of the general formulae:

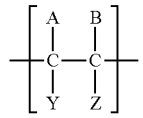

wherein A, B, Y, and Z collectively include at least two hydrophilic moieties and no hydrophobic moieties; or

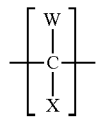

wherein W and X collectively include at least two hydrophilic moieties. Illustrative examples of such SRUs include, but are not limited to, those derived from superhydrophilic monomers described herein and the like, such as:

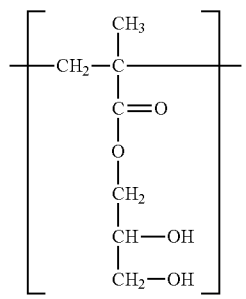

which is derived from glyceryl methacrylate; or others such as

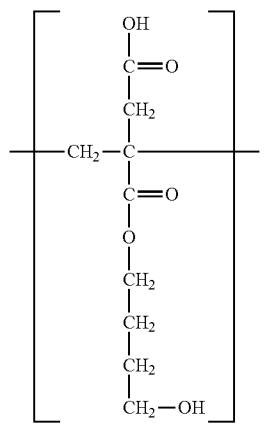

which is derived from 4-Hydroxybutyl itaconate; and the like.

Other examples of SRUs include sugar-based, monosaccharide repeat units including repeat units derived from fructose, glucose, galactose, mannose, glucosamine, mannuronic acid, guluronic acid, and the like, such as:

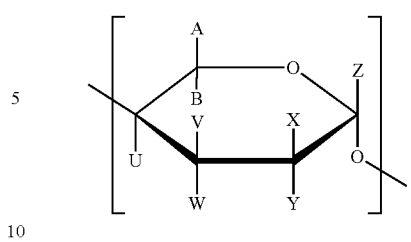

wherein A, B, U, V, W, X, Y, and Z collectively include at least two hydrophilic moieties and no hydrophobic moieties, one example of which includes

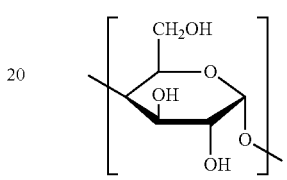

which is a α(1→4)-D-glucose SRU; or

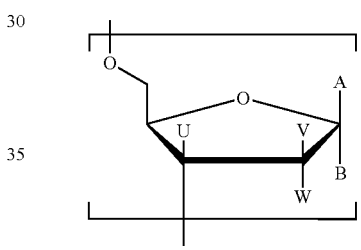

wherein A, B, U, V, and W collectively include at least two hydrophilic moieties and no hydrophobic moieties, one example of which includes

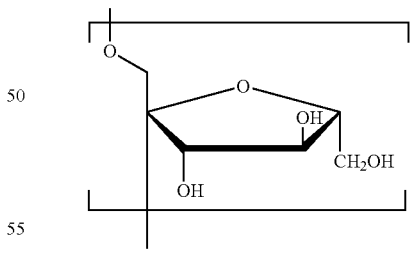

a β(2→1)-D-fructose SRU; and the like. As will be recognized by those of skill in the art, monosaccharide repeat units may be linked in various fashions, that is, through various carbons on the sugar ring e.g. (1→4), (1→6), (2→1), etc. Any of such linkages, or combinations thereof, may be suitable for use herein in monosaccharide SRUs, ARUs, or HRUs.

Other examples of SRUs include repeat units derived from amino acids, including, for example, repeat units of the formula:

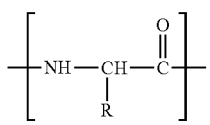

wherein R includes a hydrophilic repeat unit, examples of which include

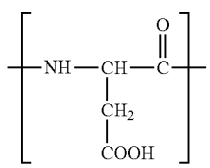

an aspartic acid SRU, and the like.

Preferred hydrophilic repeat units or superhydrophilic repeat units suitable for inclusion in the micellar thickener include ethyleneoxy, those repeat units derived from glycerol, glycidol, or glyceryl carbonate as well as those derived from hydrophilic and superhydrophilic ethylenically unsaturated monomers (e.g., acrylamide, N,N-dimethylacrylamide, acrylic acid, sodium acrylate, and sodium acryloyldmethyltaurate). Ethyleneoxy repeat units are particularly preferred. The number of hydrophilic repeat units may be from about 3 to about 1000, preferably from about 5 to about 500, more preferably from about 6 to about 400.

Hydrophobic moieties are also defined above with respect to low-DP polymerized surfactants. Preferred hydrophobic moieties suitable for inclusion in the micellar thickener are linear or branched, saturated or unsaturated alkyl or arylalkyl groups. In another preferred embodiment, the hydrophobic moiety includes adjoining repeat units or "blocks" of, for example, oxypropylene or (N-alkylacrylamide)s such as (N-t-butylacrylamide). For this embodiment in which the hydrophobic moiety includes such blocks, the number of repeat units per block is preferably from about 3 to about 400, more preferably from about 5 to about 200. By "independent hydrophobic moieties" it is meant the hydrophobic moieties do not include any common atoms, i.e., they are positioned on different portions of the micellar thickener. In a preferred embodiment, the micellar thickener is non-ionic.

The micellar thickener may include one or more linking groups that serve, for example, to covalently bond a hydrophobic moiety to a hydrophilic repeat unit. Suitable linking groups include esters, thioesters, dithioesters, carbonates, thiocarbonates, trithiocarbonates, ethers, thioethers, amides, thioamides, carbamates/urethanes and xanthates. Preferred linking groups are esters and ethers.

In certain preferred embodiments, the micellar thickener is a corona thickener, as defined above. Preferably, the independent hydrophobic moieties of the corona thickener are terminal, i.e., the hydrophobic moieties are each positioned at a separate end or terminus of different branches of the polymer.

The corona thickener may be of varying chemical configurations. One suitable configuration is a linear configuration, such as one that may be defined by the structure below:

in which HRU is a hydrophobic repeat unit having h units of HRU per mole; L and L' are linking groups; and $R_1$ and $R_2$ are hydrophobic moieties. In certain preferred embodiments, the corona thickener is a linear molecule of the above formula in which h is 3-1000, preferably 5-500, more preferably 6-400, and more preferably 10-300. A suitable example of a linear corona thickeners are a fatty acid diesters of polyethylene glycol (PEG), represented by the structure below:

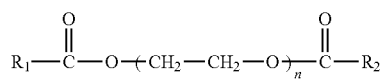

where L and L' are ester linking groups and the HRU is ethyleneoxy. One particular example of such a linear corona thickener is one in which $R_1$ and $R_2$ are $C_{17}H_{35}$ and n=150 repeat units, is PEG-150 Distearate.

Another suitable example of a linear corona thickener are fatty acid esters of an ethoxylated fatty alcohol, represented by the structure below:

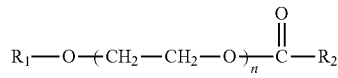

where L is an ether linking group and L' is an ester linking group and the HRU is ethyleneoxy. One particular example of such a linear corona thickener is one in which $R_1$ is $C_{24}H_{49}$ and $R_2$ is $C_{21}H_{43}$ and n=200 repeat units, is Decyltetradeceth-200 Behenate.

Another suitable corona thickener having a linear configuration is one in which the hydrophilic repeat unit combines multiple hydrophilic functionalities, such as a hydrophobically modified ethoxylated urethane (HEUR). An example of such a corona thickener is shown below:

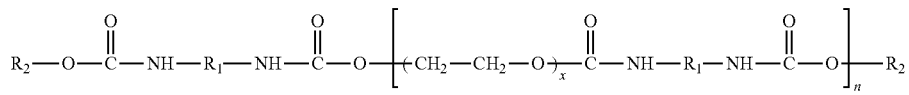

One particular example of such a HEUR is one in which $R_1$ is saturated diphenyl methylene, $R_2$ is $C_{18}H_{37}$, and x=150 repeat units, is a PEG-150/Stearyl Alcohol/SMDI Copolymer.

Yet another suitable corona thickener having a linear configuration is one in which the hydrophobic moieties comprise three or more $C_3$ or greater alkoxy groups in sequence and the hydrophilic repeat unit repeat unit includes ethylene oxide, such as a PPO-PEO-PPO block copolymer. An example of such a corona thickener is shown below:

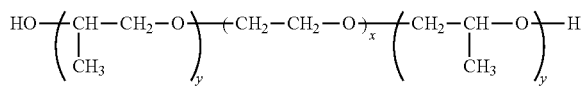

Other suitable configurations of the corona thickener are those that are branched or star-shaped in configuration. By "branched or star shaped" it is meant that the polymer includes multiple segments, e.g., 4 or 5 segments, such as those that extend from a common node structure. The node structure may be, but is not necessarily, a group of atoms that does not meet the above requirements for a hydrophobic moiety or a hydrophilic repeat unit. In one embodiment, the node structure is a branched hydrocarbon such as a neopentyl group (having 4 segments) shown below

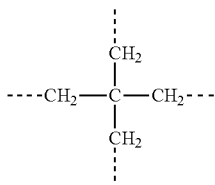

or a cyclic group such as a saccharide derived from fructose, glucose, galactose, mannose, glucosamine, mannuranic acid, gularonic acid onto which various functional groups have been reacted (an example of which, having 5 segments, is shown below).

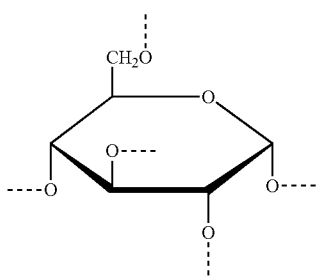

At least two of the segments that extend from the node structure include a terminal hydrophobic moiety, such as a terminal hydrophobic moiety that is joined to the node structure by an HRU. In certain embodiments, between 2 and 4 of the segments that are joined to the node structure include a terminal hydrophobic moiety, such as may be joined to the node structure by an HRU. In certain other embodiments one or more of the segments is a terminal HRU, e.g., one that is joined to the node structure, but does not form a bridge between the node structure and a terminal hydrophobic moiety.

Branched and star-shaped corona thickeners may include fatty acid polyesters of ethoxylated moieties. Suitable examples include fatty acid polyesters of ethoxylated polyglycerols. Other suitable examples include fatty acid polyesters of ethoxylated monosaccharides (e.g., fructose, glucose, galactose, mannose, glucosamine, mannuronic acid, guluronic acid). Fatty acid polyesters of ethoxylated glucosides are particularly preferred. One particular suitable example of a fatty acid polyester of an ethoxylated glucoside is a fatty acid diester of ethoxylated methyl glucoside, as represented by the structure below:

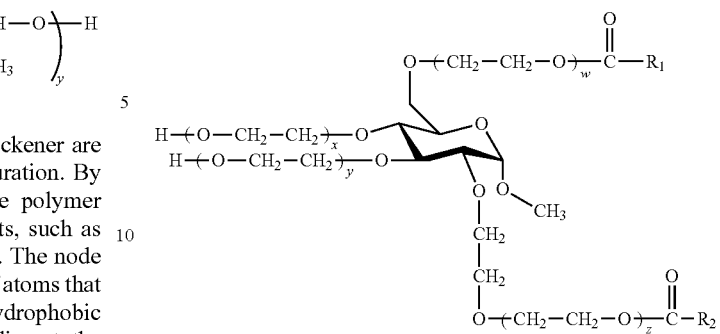

in which 4 distinct hydrophilic segments (here, each are comprised of ethyleneoxy HRUs) are linked via ether linkages to a methyl glucoside nodal structure. Two of the ethyleneoxy segments are also linked via an ester linking group to terminal fatty acid hydrophobic moieties. Thus, this particular corona thickener has 5 segments, two of these five include independent terminal hydrophobic moieties. Two of the remaining segments are terminal HRUs joined to the node structure via an ether linkage. One particular example of such a corona thickener is one in which the sum of the number of ethyleneoxy repeat units, $w+x+y+z=119$ and $R_1$ and $R_2$ are $C_{17}H_{33}$ (oleate), is PEG-120 Methyl Glucose Dioleate, sold commercially as Antil 120 Plus by Evonik. Other examples of suitable materials comprise ethoxylated methyl glucoside fatty acid esters of the structure below:

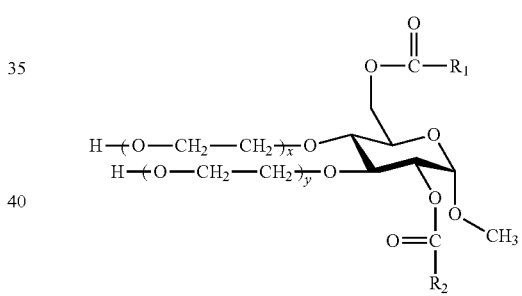

An example of such a material includes PEG-120 Methyl Glucose Dioleate, where $x+y=120$, $R_1=R_2=C_{17}H_{33}$, sold commercially as Glucamate DOE-120 by Lubrizol.

Another suitable fatty acid polyester of an ethoxylated glucoside is a fatty acid triester of ethoxylated methyl glucoside, as represented by the structure below:

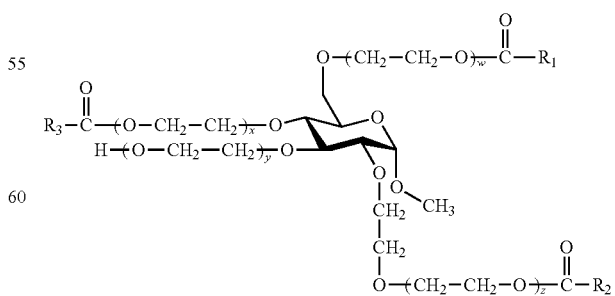

in which 4 distinct hydrophilic segments (here, each are comprised of HRUs) are linked via ether linkages to a methyl glucoside nodal structure. Three of the polyethyleneoxy segments are also linked via an ester linking group to terminal fatty acid hydrophobic moieties, and the fourth polyethyleneoxy segment terminates with a hydroxyl group. Thus, this particular corona thickener has 5 segments, three of these five include independent terminal hydrophobic moieties. One of the remaining segments is a terminal HRU joined to the node structure via an ether linkage. One particular example of such a corona thickener is one in which the sum of the number of ethyleneoxy repeat units, w+x+y+z=119 and $R_1$ and $R_2$ are $C_{17}H_{33}$ (oleate), is PEG-120 Methyl Glucose Trioleate. Other examples of suitable materials comprise fatty acid esters of ethoxylated methyl glucoside fatty acid esters of the formula below:

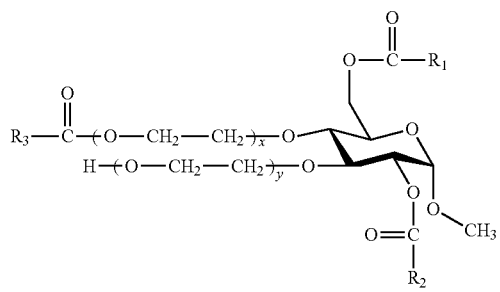

An example of such a material includes PEG-120 Methyl Glucose Trioleate, where x+y=120, $R_1$=$R_2$=$R_3$=$C_{17}H_{33}$, sold commercially as Glucamate LT by Lubrizol.

Another suitable example of corona thickener having a branched (or star-shaped) configuration is one having 4 segments. The 4 segments may each include an independent hydrophobic moiety. These may be joined to the node structure via HRUs. An example of a branched or star shaped corona thickener having 4 segments, a fatty acid nolvester of a star shaved PEG, is represented by the structure below:

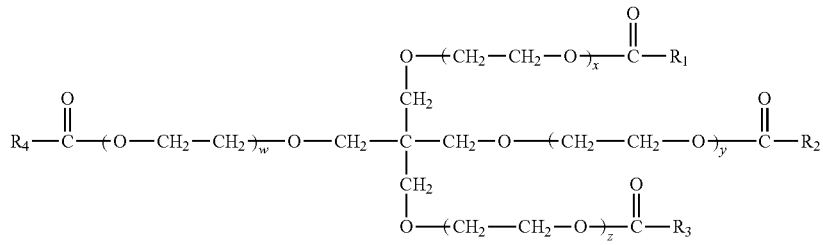

in which 4 distinct hydrophilic segments (here, each are comprised of ethyleneoxy repeat units) are linked via ether linkages to a nodal structure. The nodal structure consists of a pentaerythrityl functionality (i.e. a quaternary carbon atom having four pendant $CH_2$ groups bonded thereto). All four of the polyethyleneoxy segments are also linked via an ester linking group to terminal fatty acid hydrophobic moieties.

One particular example of such a corona thickener is one in which the sum of the number of ethyleneoxy repeat units, w+x+y+z=150 and $R_1$, $R_2$, $R_3$, and $R_4$ are $C_{17}H_{35}$, is PEG-150 Pentaerythrytyl Tetrastearate.

Another suitable example of corona thickener having a star-shaped configuration is a PEO-PPO star block copolymer. A suitable structure is provided below:

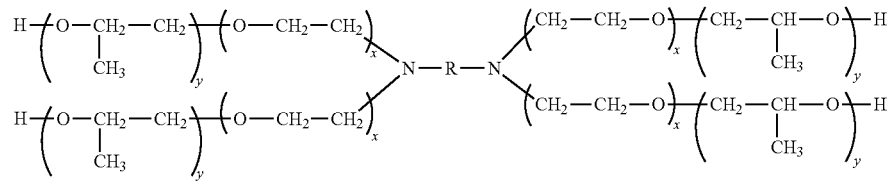

In the corona thickener shown above, N—R—N represents a nodal structure from which four segments emanate. R may be, for example an ethyl group, —$CH_2CH_2$—. Each branch includes an ethyleneoxy segment of x repeat units and terminates with a poly(oxypropylene) hydrophobic block.

In certain embodiments, the micellar thickener is a core thickener, as defined above. Suitable core thickeners have a linear or branched configuration. Examples of branched core thickeners include those derived from glycerol. One suitable example of a branched core thickener derived from glycerol is a glyceryl fatty acid ester, such as those defined by the structure below: e $$R-\overset{O}{\underset{\|}{C}}-O-CH_2-\underset{\underset{OH}{|}}{CH}-CH_2-OH$$

One particular example is glyceryl oleate, in which R=$C_{17}H_{33}$.

Another example of a branched core thickener derived from glycerol is a polyglycerol, such as polyglyceryl fatty acid esters, such as such as those defined by the structure below in which one of the hydrophilic moieties is positioned in an HRU:

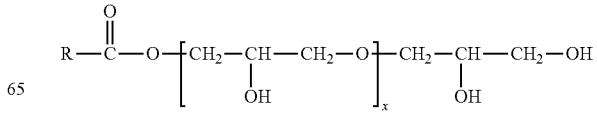

One particular example is polyglyceryl-10 oleate where $R=C_{17}H_{33}$ and $x=9$ (Polyaldo 10-1-O, available from Lonza Group LLC, Basel Switzerland).

Yet another example of suitable core thickeners include fatty acid mono and dialkanolamides, such as those defined by the structure below:

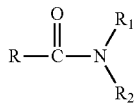

One particular example is lauramide DEA, where $R=C_{11}H_{23}$ and $R_1=R_2=CH_2CH_2OH$.

Yet another example of suitable core thickeners include fatty acid esters of sorbitan, such as those defined by the structure below:

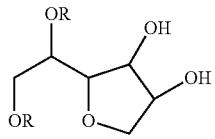

One particular example is sorbitan sesquicaprylate (available as Antil SC from Evonik Industries AG Dusseldorf, Germany), where $R=C_7H_{15}CO$ or H with average 1.5 mol $C_7H_{15}CO$ per mol sorbitan.

Any amounts of micellar thickeners suitable to increase viscosity of compositions of the present invention may be combined according to the present methods. For example, micellar thickener may be included in an amount in the formulation sufficient to increase the viscosity of the composition at least about 100 cP (when tested according to the Formulation Viscosity Test, described below), preferably sufficient to raise the viscosity at least about 200 cP, more preferably sufficient to raise the viscosity at least about 500 cP, even more preferably sufficient to raise the viscosity at least about at least about 1000 cP. The increases in viscosity specified above are as when compared with a composition which has water substituted for the micellar thickener.

According to certain embodiments, the micellar thickener is used in a concentration from greater than about 0.1% to about 15% by weight of active micellar thickener in the composition. Preferably, the micellar thickener is in a concentration from about 0.1 to about 10%, more preferably from about 0.1% to about 5%, even more preferably from about 0.2% to about 4%, even more preferably from about 0.5% to about 4%, and most preferably from about 1% to about 4% of active micellar thickener in the composition.

Compositions useful in the present invention may also include any of a variety of monomeric surfactants. By "monomeric surfactants" it is meant any surface active agents that do not meet the definition of "polymerized surfactant" as defined above. The monomeric surfactants may be anionic, nonionic, amphoteric or cationic, examples of which are detailed below.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

alkyl ether sulfates of the formula

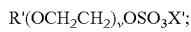

alkyl monoglyceryl ether sulfates of the formula

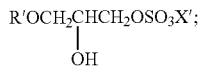

alkyl monoglyceride sulfates of the formula

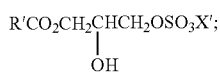

alkyl monoglyceride sulfonates of the formula

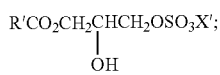

alkyl sulfonates of the formula

alkylaryl sulfonates of the formula

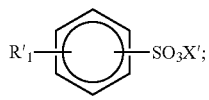

alkyl sulfosuccinates of the formula:

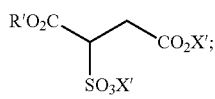

alkyl ether sulfosuccinates of the formula:

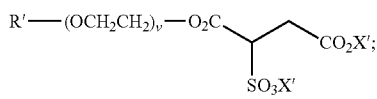

alkyl sulfosuccinamates of the formula:

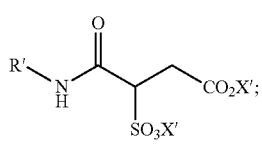

alkyl amidosulfosuccinates of the formula

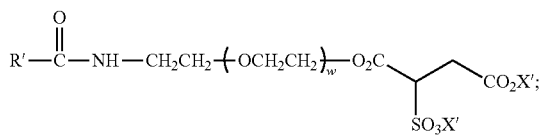

alkyl carboxylates of the formula:

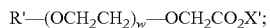

alkyl amidoethercarboxylates of the formula:

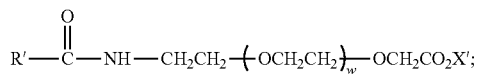

alkyl succinates of the formula:

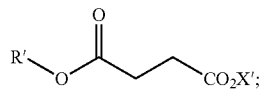

fatty acyl sarcosinates of the formula:

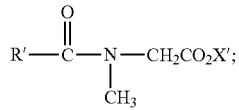

fatty acyl amino acids of the formula:

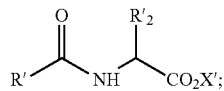

fatty acyl taurates of the formula:

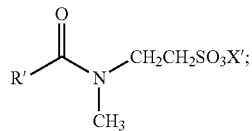

fatty alkyl sulfoacetates of the formula:

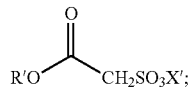

alkyl phosphates of the formula:

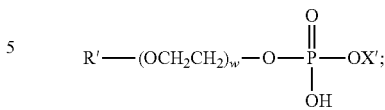

wherein

R' is an alkyl group having from about 7 to about 22, and preferably from about 7 to about 16 carbon atoms, $R'_1$ is an alkyl group having from about 1 to about 18, and preferably from about 8 to about 14 carbon atoms, $R'_2$ is a substituent of a natural or synthetic I-amino acid, X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and v is an integer from 1 to 6;

w is an integer from 0 to 20;

and mixtures thereof.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, a-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Croda, Inc. of Edison, N.J. under the tradename, "Atlas G-4280." Polysorbate 20, which is the laurate monoester of a mixture of sorbitol and sorbitol anhydrides condensed with approximately 20 moles of ethylene oxide, is available commercially from Croda, Inc. of Edison, N.J. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Cognis Corporation of Ambler, Pa. under the tradename, "Plantaren 2000."

Any of a variety of amphoteric surfactants are suitable for use in the present invention. As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

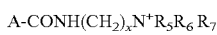

wherein

A is an alkyl or alkenyl group having from about 7 to about 21, e.g. from about 10 to about 16 carbon atoms;

x is an integer of from about 2 to about 6;

$R_5$ is hydrogen or a carboxyalkyl group containing from about 2 to about 3 carbon atoms;

$R_6$ is a hydroxyalkyl group containing from about 2 to about 3 carbon atoms or is a group of the formula:

$R_8$—O—$(CH_2)_n$$CO_2^-$ wherein $R_8$ is an alkylene group having from about 2 to about 3 carbon atoms and n is 1 or 2; and $R_7$ is a carboxyalkyl group containing from about 2 to about 3 carbon atoms;

Examples of suitable alkyl betaines include those compounds of the formula:

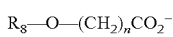

wherein

B is an alkyl or alkenyl group having from about 8 to about 22, e.g., from about 8 to about 16 carbon atoms;

$R_9$ and $R_{10}$ are each independently an alkyl or hydroxyalkyl group having from about 1 to about 4 carbon atoms; and p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

wherein

D is an alkyl or alkenyl group having from about 7 to about 21, e.g. from about 7 to about 15 carbon atoms;

$R_{11}$ and $R_{12}$ are each independently an alkyl or Hydroxyalkyl group having from about 1 to about 4 carbon atoms;

q is an integer from about 2 to about 6; and m is 1 or 2.

One amidoalkyl betaine is cocamidopropyl betaine, available commercially from Evonik Industries of Hopewell, Va. under the tradename, "Tegobetaine L7."

Examples of suitable amidoalkyl sultaines include those compounds of the formula

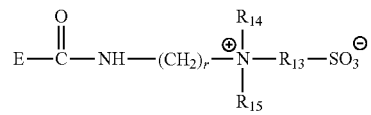

wherein

E is an alkyl or alkenyl group having from about 7 to about 21, e.g. from about 7 to about 15 carbon atoms;

$R_{14}$ and $R_{15}$ are each independently an alkyl, or hydroxyalkyl group having from about 1 to about 4 carbon atoms;

r is an integer from about 2 to about 6; and $R_{13}$ is an alkylene or hydroxyalkylene group having from about 2 to about 3 carbon atoms;

In one embodiment, the amidoalkyl sultaine is cocamidopropyl hydroxysultaine, available commercially from Rhodia Novecare of Cranbury, N.J. under the tradename, "Mirataine CBS."

Examples of suitable amphophosphate compounds include those of the formula:

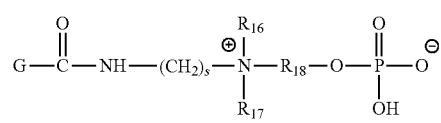

wherein

G is an alkyl or alkenyl group having about 7 to about 21, e.g. from about 7 to about 15 carbon atoms;

s is an integer from about 2 to about 6;

$R_{16}$ is hydrogen or a carboxyalkyl group containing from about 2 to about 3 carbon atoms;

$R_{17}$ is a hydroxyalkyl group containing from about 2 to about 3 carbon atoms or a group of the formula:

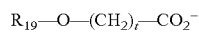

wherein $R_{19}$ is an alkylene or hydroxyalkylene group having from about 2 to about 3 carbon atoms and t is 1 or 2; and $R_{18}$ is an alkylene or hydroxyalkylene group having from about 2 to about 3 carbon atoms.

In one embodiment, the amphophosphate compounds are sodium lauroampho PG-acetate phosphate, available commercially from Croda, Inc. of Edison, N.J. under the tradename, "Monateric 1023," and those disclosed in U.S. Pat. No. 4,380,637, which is incorporated herein by reference.

Examples of suitable phosphobetaines include those compounds of the formula:

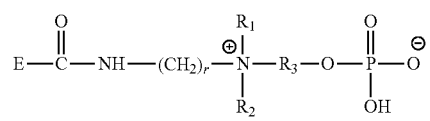

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

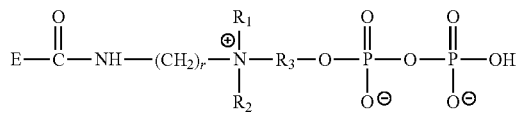

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

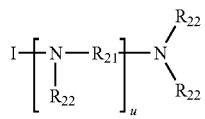

wherein
- I is an alkyl or alkenyl group containing from about 8 to about 22, e.g. from about 8 to about 16 carbon atoms;
- $R_{22}$ is a carboxyalkyl group having from about 2 to about 3 carbon atoms;
- $R_{21}$ is an alkylene group having from about 2 to about 3 carbon atoms and
- u is an integer from about 1 to about 4.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any amounts of monomeric surfactant suitable to produce low small micelle fraction composition may be combined according to the present methods. For example, the amount of monomeric surfactants used in the present invention may be from about 0.1 to about 30%, more preferably from about 0.5 to about 20%, even more preferably from about 1 to about 15% of total active monomeric surfactant in the composition, and even more preferably from about 2% to about 10%.

Any relative amounts of polymerized surfactants and monomeric surfactant suitable to produce low small micelle fraction composition may be combined according to the present methods. According to certain embodiments, the compositions comprise a ratio of low-DP polymerized surfactant to the sum total of all monomeric surfactants of from about 0.1:1 to about 5:1, and preferably from about 0.25:1 to about 3:1.

The compositions of the present invention may comprise any of a variety of additional other ingredients used conventionally in healthcare/personal care compositions ("personal care components"). These other ingredients nonexclusively include one or more, pearlescent or opacifying agents, thickening agents, emollients, secondary conditioners, humectants, chelating agents, actives, exfoliants, and additives which enhance the appearance, feel and fragrance of the compositions, such as colorants, fragrances, preservatives, pH adjusting agents, and the like.

Any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof The pearlescent or opacifying agent may be introduced to the mild cleansing composition as a pre-formed, stabilized aqueous dispersion, such as that commercially available from Cognis Corporation of Ambler, Pa. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and may be in a weight percent ratio of from about 25 to about 30: about 3 to about 15: about 20 to about 25, respectively.

Compositions useful in the present invention may also include any of a variety of conventional thickeners that do not meet the requirements specified above in order to be considered micellar thickeners. Examples of suitable conventional thickeners include various thickeners having molecular weights of greater than about 100,000 grams per mole, including chemistries such as: hydroxyalkyl cellulose; alkyl cellulose; hydroxyalkyl alkyl cellulose; xanthan and guar gums, succinoglycan gums; and mixtures thereof.

Any of a variety of commercially available secondary conditioners, such as volatile silicones, which impart additional attributes, such as gloss to the hair are suitable for use in this invention. The volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable secondary conditioners include cationic polymers, including polyquarterniums, cationic guar, and the like.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, polyglycerols, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include, for example, parabens, quaternary ammonium species, phenoxyethanol, benzoates, DMDM hydantoin, and are present in the composition in an amount, based upon the total weight of the composition, from about 0 to about 1 percent or from about 0.05 percent to about 0.5 percent.

The low-DP polymerized surfactant, optional monomeric surfactants and optional other components of the composition may be combined according to the present invention via any conventional methods of combining two or more fluids or solids. For example, one or more compositions comprising, consisting essentially of, or consisting of at least one low-DP polymerized surfactant and one or more compositions comprising, consisting essentially of, or consisting of one or more micellar thickeners, and one or more compositions comprising, consisting essentially of, or consisting of water, monomeric surfactants or suitable ingredients may be combined by pouring, mixing, adding dropwise, pipetting, pumping, and the like, one of the compositions comprising the polymerized surfactant and one of the compositions comprising the micellar thickener into or with the other in any order using any conventional equipment such as a mechanically stirred propeller, paddle, and the like.

The methods of the present invention may further comprise any of a variety of steps for mixing or introducing one or more of the optional components described hereinabove with or into a composition comprising a low-DP polymerized surfactant either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising the polymerized surfactant.

The pH of the present compositions is not critical, but may be in a range that does not facilitate irritation to the skin, such as from about 4 to about 7. The viscosity of the personal care composition is not critical, although it may be a spreadable cream or lotion or gel. In certain embodiments, the personal care composition has a viscosity from about 200 cP to about 10,000 cP, such as when evaluated according to the Formulation Viscosity Test, as described below.

Personal care compositions of the present invention are general capable of providing a high degree of flash foam. Applicants have characterized a particularly helpful way of measuring the effectiveness of flash foam performance is to measure the rate at which foam volume develops as a function of rotation cycles of a container, as measured using the Formulation Flash Foam Test described below. In certain embodiments, the personal care compositions of the present invention have a foam generation rate, FGR, as measured using the Formulation Flash Foam Test, that is at least about 10 mL/cycle, preferably at least about 15 mL/cycle, more preferably at least about 20 mL/cycle.

The compositions useful in the present invention involve formulations suitable for administering to the target tissues, such as mammalian skin such as human skin. In one embodiment, the composition comprises a low-DP polymerized surfactant and a carrier, preferably a cosmetically-acceptable carrier. As used herein, the term "cosmetically-acceptable carrier" means a carrier that is suitable for use in contact with the skin without undue toxicity, incompatibility, instability, irritation, allergic response, and the like. This term is not intended to limit the carrier for use solely as a cosmetic (e.g., the ingredient/product can be used as a pharmaceutical).

The compositions may be made into a wide variety of product types that include but are not limited to cleansing liquid washes, gels, sticks, sprays, solid bars, shampoos, pastes, foams, powders, mousses, shaving creams, wipes, patches, nail lacquers, wound dressing and adhesive bandages, hydrogels, films and make-up such as foundations, mascaras, and lipsticks. These product types may comprise several types of cosmetically-acceptable carriers including, but not limited to solutions, emulsions (e.g., microemulsions and nanoemulsions), gels, and solids. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof. In certain preferred embodiments, the compositions of the present invention are aqueous solutions comprising from about 50% to about 99% by weight of water.

According to certain embodiments, compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32 43 (1972) and the International Cosmetic Ingredient Dictionary and Handbook, eds. Wenninger and McEwen, pp. 1656 61, 1626, and 1654 55 (The Cosmetic, Toiletry, and Fragrance Assoc., Washington, D.C., 7.sup.th Edition, 1997) (hereinafter "ICI Handbook") contains numerous examples of suitable materials. A lotion can be made from such a solution. Lotions typically comprise from about 1% to about 20% (e.g., from about 5% to about 10%) of an emollient(s) and from about 50% to about 90% (e.g., from about 60% to about 80%) of water.

The present compositions may be of varying phase compositions, but are preferably aqueous solutions or otherwise include an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

In certain embodiments, the compositions produced via the present invention are preferably used as or in personal care products for treating or cleansing at least a portion of a mammalian body, for example, the human body. Examples of certain preferred personal care products include various products suitable for application to the skin, hair, oral and/or perineal region of the body, such as shampoos, hand, face, and/or body washes, bath additives, gels, lotions, creams, and the like. As discussed above, applicants have discovered unexpectedly that the instant methods provide personal care products having reduced irritation to the skin and/or eyes and, in certain embodiments one or more of desirable properties such as flash foaming characteristics, rheology, and functionality, even at high surfactant concentrations. Such products may further include a substrate onto which a composition is applied for use on the body. Examples of suitable substrates include a wipe, pouf, sponge, and the like as well as absorbent articles, such as a bandage, sanitary napkin, tampon, and the like.

The present invention provides methods of treating and/or cleansing the human body comprising contacting at least a portion of the body with a composition of the present invention. Certain preferred methods comprising contacting mammalian skin, hair and/or vaginal region with a composition of the present invention to cleanse such region and/or treat such region for any of a variety of conditions including, but not limited to, acne, wrinkles, dermatitis, dryness, muscle pain, itch, and the like. In certain preferred embodiments, the contacting step comprises applying a composition of the present invention to human skin, hair or vaginal region.

The cleansing methods of the present invention may further comprise any of a variety of additional, optional steps associated conventionally with cleansing hair and skin including, for example, lathering, rinsing steps, and the like.

EXAMPLES

Formulation Viscosity Test:

The following Viscosity Test was performed on various personal care compositions to determine the viscosity according to the present invention. Viscosities of test formulations were conducted at 25° C. using a Brookfield DV-I+ viscometer (Brookfield Engineering Laboratories, Inc. Middleboro, Mass.). Measurement parameters are selected so as to ensure "% torque" is between 40%-60% on the viscometer. Typical operating parameters are spindle #S62 operating at six rpm. One skilled in the art will recognize that in order to accommodate samples of higher viscosities, it may be necessary to change spindle selection or operating speed to enable a viscosity measurement.

Formulation Flash Foam Test:

The following Formulation Flash Foam Test was performed on various personal care compositions to determine the foam volume as a function of agitation, according to the present invention. To a bottom of a clean, dry 500 mL Pyrex glass graduated mixing cylinder was charged 50 g of test formulation. Deionized water (50 g) was then slowly and carefully poured down the side of the flask, with care taken to avoid mixing with the test formulation, so as to form a separate layer of water on top of the test formulation. The cylinder was fitted with a stopper secured with Parafilm and mounted in the Vertical Rotator Assembly of a Gaum Foam Machine (Gaum Inc., Robbinsville, N.J.). The cylinder was rotated at cycle speed #30 for a total of 20 cycles. The foam volume was recorded at two cycle intervals by stopping rotation and reading the foam volume on the graduated cylinder. The height of the foam was measured at the level where the foam bubbles are dense enough to render the graduated cylinder opaque. The Formulation Flash Foam Value was reported as the average of two individual runs. The Foam Generation Rate, FGR, was calculated by plotting Formulation Flash Foam Value as a function of shake cycle (2 cycles to 20 cycles) and fitting the data to a straight line function. The FGR is the slope of the resulting linear fit.

Examples E1-E8

Preparation of Inventive Personal Care Compositions and Measurement of Formulation Viscosity The following personal care compositions, Inventive Examples E1-E8, and were prepared and tested for Formulation Viscosity. Each of Inventive Examples E1-E2 included a low-DP polymerized surfactant (PA-18) and a corona thickener (Glucamate DOE-120 or Glucamate LT).

TABLE 1

| Tradename | INCI Name | Ex. 1 | Ex. 2 |
|---|---|---|---|
| PA-18 LV | Octadecene/MA Copolymer | 4.50 | 4.50 |
| Sodium Hydroxide pellets | Sodium Hydroxide | 1.13 | 1.13 |
| Tegobetaine L7-V (30%) | Cocamidopropyl Betaine | 15.00 | 15.00 |
| Emery 917 | Glycerin | 5.00 | 5.00 |
| Glucamate DOE-120 | PEG-120 Methyl Glucose Dioleate | 2.20 | — |
| Glucamate LT | PEG-120 Methyl Glucose Trioleate (and) Propylene Glycol (and) Water | — | 4.00 |
| Versene 100XL (50%) | Tetrasodium EDTA | 1.00 | 1.00 |
| Glydant (55%) | DMDM Hydantoin | 0.50 | 0.50 |
| Fragrance | Fragrance | 0.20 | 0.20 |
| Sodium Hydroxide solution (20%) | Sodium Hydroxide | q.s. | q.s. |
| Citric Acid solution (20%) | Citric Acid | q.s. | q.s. |
| Purified Water | Water | q.s. | q.s. |
| | Viscosity (cP) | 9000 | 11940 |

The following procedure is employed to prepare Inventive Examples Ex. 1 and Ex. 2: to an appropriately sized vessel equipped with a hotplate and overhead mechanical stirrer, 60 parts Water was added. While mixing at 200-250 rpm and heating to 85-90° C., Sodium Hydroxide pellets and Octadecene/MA Copolymer were added. The batch was mixed at 85-90° C. until all Octadecene/MA Copolymer was dissolved, indicating completion of hydrolysis and neutralization. The batch was allowed to cool to 65-70° C. while mixing, and Glycerin and PEG-120 Methyl Glucose Dioleate were then added. The batch was mixed at 65-70° C. until all PEG-120 Methyl Glucose Dioleate was dissolved. Upon complete dissolution of all PEG-120 Methyl Glucose Dioleate, heating was stopped and the batch was allowed to cool to 50° C. while mixing at 200-250 rpm. At 50° C., Cocamidopropyl Betaine was added to the batch, and the batch was allowed to cool below 40° C., at which point Tetrasodium EDTA, DMDM Hydantoin, and Fragrance were added. The batch was allowed to mix while cooling to below 30° C. and was then adjusted to pH 6.7-7.2 (target pH=6.9) using necessary amounts of Citric Acid and/or Sodium Hydroxide. Water was added in q.s. to 100 wt %, and the batch was allowed to mix until uniform before being discharged to an appropriate storage vessel.

As is apparent from Table 1, that micellar thickeners can be combined with low-DP polymerized surfactants to achieve varying viscosities.

Examples E3-E6

Preparation of Inventive Personal Care Compositions and Measurement of Formulation Viscosity The following personal care compositions, Inventive Examples E9-E12 and were prepared and tested for Formulation Viscosity.

TABLE 2

| Tradename | INCI Name | Ex. 3 | Ex. 4 | Ex. 5 | Ex. 6 |
|---|---|---|---|---|---|
| PA-18 LV | Octadecene/MA Copolymer | 4.50 | 4.50 | 4.50 | 4.50 |
| Sodium Hydroxide pellets | Sodium Hydroxide | 1.13 | 1.13 | 1.13 | 1.13 |
| Tegobetaine L7-V (30%) | Cocamidopropyl Betaine | 15.00 | 15.00 | 15.00 | 15.00 |
| Emery 917 | Glycerin | 5.00 | 5.00 | 5.00 | 5.00 |
| Glucamate DOE-120 | PEG-120 Methyl Glucose Dioleate | 1.00 | 2.20 | 4.00 | 5.32 |
| Versene 100XL (50%) | Tetrasodium EDTA | 1.00 | 1.00 | 1.00 | 1.00 |
| Glydant (55%) | DMDM Hydantoin | 0.50 | 0.50 | 0.50 | 0.50 |
| Fragrance | Fragrance | 0.20 | 0.20 | 0.20 | 0.20 |
| Sodium Hydroxide solution (20%) | Sodium Hydroxide | q.s. | q.s. | q.s. | q.s. |
| Citric Acid solution (20%) | Citric Acid | q.s. | q.s. | q.s. | q.s. |
| Purified Water | Water | q.s. | q.s. | q.s. | q.s. |
| | Viscosity (cP) | 1568 | 9000 | 25160 | 38240 |

Inventive Examples, Ex. 3-Ex. 6 were prepared in a manner similarly to Inventive Examples Ex. 1-Ex. 2. As is apparent from Table 2, by increasing the concentration of PEG-120 Methyl Glucose Dioleate, one is able to increase the viscosity of a composition that includes PA-18 from, for example, about 1568 cP to about 38240 cP.

Comparative Example C1

Preparation of Comparative Personal Care Compositions and Measurement of Formulation Viscosity The following personal care composition, Comparative Example C1 was prepared and tested for Formulation Viscosity.

TABLE 3

| Tradename | INCI Name | C 1 |
|---|---|---|
| PA-18 LV | Octadecene/MA Copolymer | 4.50 |
| Sodium Hydroxide pellets | Sodium Hydroxide | 1.13 |
| Tegobetaine L7-V (30%) | Cocamidopropyl Betaine | 15.00 |
| Emery 917 | Glycerin | 5.00 |
| Carbopol AQUA SF-1 (30%) | Acrylates Copolymer | 7.00 |
| Versene 100XL (50%) | Tetrasodium EDTA | 1.00 |
| Glydant (55%) | DMDM Hydantoin | 0.50 |
| Fragrance | Fragrance | 0.20 |
| Sodium Hydroxide solution (20%) | Sodium Hydroxide | q.s. |
| Citric Acid solution (20%) | Citric Acid | q.s. |
| Purified Water | Water | q.s. |
| | Viscosity (cP) | 9300 |

Comparative Example, C1 was prepared in a similar manner to the previous Inventive Example, Ex. 1, except that CARBOPOL AQUA SF-1 (a conventional, high molecular weight, "alkali-swellable emulsion polymeric thickener") was substituted for PEG-120 Methyl Glucose Dioleate. The Formulation Viscosity was measured to be 9300 cP (reasonably close to Inventive Example, Ex. 1).

Comparison of Formulation Flash Foam Values for Personal Care Compositions

Inventive Example, Ex. 1 and Comparative Example C1 were tested for Formulation Flash Foam Value using the Formulation Flash Foam Test described above. The data is shown in Table 4 below. The two data sets (one for Comparative Example C1 and the other for Inventive Example, Ex. 1) are also shown in FIG. 1.

TABLE 4

| | Foam Volume of C1 (mL) | | | | Foam Volume of Ex 1 (mL) | | | |
|---|---|---|---|---|---|---|---|---|
| Cycles | Run 1 | Run 2 | Avg | Std Dev | Run 1 | Run 2 | Avg | Std Dev |
| 2 | 120 | 115 | 118 | 4 | 120 | 110 | 115 | 7 |
| 4 | 145 | 145 | 145 | 0 | 150 | 160 | 155 | 7 |
| 6 | 160 | 175 | 168 | 11 | 190 | 210 | 200 | 14 |
| 8 | 200 | 210 | 205 | 7 | 225 | 260 | 243 | 25 |
| 10 | 215 | 235 | 225 | 14 | 290 | 310 | 300 | 14 |
| 12 | 240 | 260 | 250 | 14 | 315 | 350 | 333 | 25 |
| 14 | 260 | 275 | 268 | 11 | 360 | 380 | 370 | 14 |
| 16 | 275 | 300 | 288 | 18 | 400 | 425 | 413 | 18 |
| 18 | 300 | 325 | 313 | 18 | 415 | 450 | 433 | 25 |
| 20 | 315 | 350 | 333 | 25 | 440 | 475 | 458 | 25 |

As can be readily seen in Table 4, Inventive Example, Ex. 1 essentially develops greater flash foam, e.g., a higher amount of foam than Comparative Example, C1, when compared at most points (number of cycles) during the test. Inventive Example, Ex. 1 also reaches a terminal foam volume at 20 cycles that is 36% higher than that of Comparative Example, C1 (458 compared with 333). Furthermore, as can be seen in FIG. 1, the Foam Generation Rate, FGR, for Inventive Example, Ex. 1 is about 66% higher than that of Comparative Example, C1 (19.705 compared with 11.879). Applicants attribute this superiority in performance of the Inventive Examples to the dramatic improvement in the micellar thickener-thickened formula to "break" and lose viscosity upon dilution. By comparison, the low-DP polymerized surfactant-containing compositions that are thickened with the conventional high molecular weight alkali-swellable emulsion polymeric thickeners do not readily "break" upon dilution and are relatively poor flash foamers.

We claim:

1. A healthcare composition comprising a low-DP polymerized surfactant that is a PPDA, a micellar thickener selected from the group consisting of corona thickeners comprising two or more linear $C_{18}$-$C_{24}$ hydrophobic moieties and corona thickeners that are fatty acid esters of ethoxylated fatty alcohols, and a cosmetically-acceptable carrier.

2. The healthcare composition of claim 1, wherein the low-DP polymerized surfactant has a weight average molecular weight that is from about 3500 to about 500,000.

3. The healthcare composition of claim 1, wherein the low-DP polymerized surfactant has a weight average molecular weight that is from about 5000 to about 200,000.

4. The healthcare composition of claim 1, wherein the low-DP polymerized surfactant has a PMOD% that is less than about 90%.

5. The healthcare composition of claim 1, wherein the low-DP polymerized surfactant has a PMOD% that is less than about 80%.

6. The healthcare composition of claim 1, further comprising at least one monomeric surfactant.

7. The healthcare composition of claim 1, wherein the corona thickener has from about 3 to about 1000 hydrophilic repeat units on a weight average basis.

8. The healthcare composition of claim 7, wherein the corona thickener is characterized by the following structure:

in which HRU is a hydrophobic repeat unit, $R_1$ and $R_2$ are hydrophobic moieties, L and L' are moieties selected from the group consisting of esters, thioesters, dithioesters, carbonates, thiocarbonates, trithiocarbonates, ethers, thioethers, amides, thioamides, carbamates/urethanes and xanthates, and h is from 3-1000.

9. The healthcare composition of claim 7, wherein the corona thickener is a fatty acid ester of a polyethylene glycol or a fatty acid ester of an ethoxylated fatty alcohol.

10. The healthcare composition of claim 7, wherein the corona thickener is a fatty acid polyester of an ethoxylated glucoside.

11. The healthcare composition of claim 7, wherein the corona thickener has from about 5 to about 500 hydrophilic repeat units on a weight average basis.

12. The healthcare composition of claim 1, wherein the micellar thickener is linear.

13. The healthcare composition of claim 1, wherein the healthcare composition has a foam generation rate of at least about 15 mL/cycle.

14. The healthcare composition of claim 1, wherein the micellar thickener is present in an amount sufficient to increase the viscosity of the composition at least about 100 cP.

15. The healthcare composition of claim 1, wherein the micellar thickener has a branched or star-shaped configuration.

16. The healthcare composition of claim 1, wherein the micellar thickener is glycerol-based.

17. The healthcare composition of claim 1, wherein the PPDA is derived via hydrolysis of 1:1 alternating copolymers of maleic anhydride.

* * * * *